(12) United States Patent
Vardanega

(10) Patent No.: US 7,879,078 B2
(45) Date of Patent: Feb. 1, 2011

(54) USE OF CONVECTIVE AIR WARMING SYSTEM FOR PATIENT CARE

(75) Inventor: Michael Vardanega, Livermore, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1107 days.

(21) Appl. No.: 11/527,866

(22) Filed: Sep. 27, 2006

(65) Prior Publication Data

US 2008/0077207 A1    Mar. 27, 2008

(51) Int. Cl.
*A61F 7/00* (2006.01)
*A61F 7/08* (2006.01)

(52) U.S. Cl. .................. 607/104; 607/107; 607/108; 128/849

(58) Field of Classification Search .......... 607/104, 607/107, 108; 128/849
See application file for complete search history.

(56) References Cited

U.S. PATENT DOCUMENTS

| | | | | |
|---|---|---|---|---|
| 2,941,907 A * | 6/1960 | Tousignant et al. | ......... | 131/332 |
| 3,060,932 A * | 10/1962 | Pereny et al. | ......... | 128/849 |
| 3,236,370 A * | 2/1966 | Pereny et al. | ......... | 206/440 |
| 3,410,266 A * | 11/1968 | Krzewinski et al. | ......... | 128/849 |
| 3,667,458 A * | 6/1972 | Krebs | ......... | 128/853 |
| 3,741,206 A * | 6/1973 | Binard et al. | ......... | 128/853 |
| 3,750,664 A * | 8/1973 | Collins | ......... | 128/853 |
| 3,835,851 A * | 9/1974 | Villari | ......... | 128/853 |
| 3,916,887 A * | 11/1975 | Kelly | ......... | 128/851 |
| 4,024,862 A * | 5/1977 | Collins | ......... | 128/854 |
| 4,089,331 A * | 5/1978 | Hartigan et al. | ......... | 128/850 |
| 4,334,529 A * | 6/1982 | Wirth | ......... | 128/852 |
| 4,807,644 A * | 2/1989 | Sandhaus | ......... | 128/849 |
| 4,957,120 A * | 9/1990 | Grier-Idris | ......... | 128/849 |
| 5,265,599 A * | 11/1993 | Stephenson et al. | ......... | 607/104 |
| 5,443,488 A * | 8/1995 | Namenye et al. | ......... | 607/104 |
| 5,545,194 A * | 8/1996 | Augustine | ......... | 607/104 |
| 5,728,145 A * | 3/1998 | Phlipot et al. | ......... | 607/104 |
| 5,735,890 A * | 4/1998 | Kappel et al. | ......... | 607/104 |
| 5,817,147 A * | 10/1998 | Wolf | ......... | 607/104 |
| 5,832,925 A * | 11/1998 | Rothrum | ......... | 128/849 |
| 5,890,243 A * | 4/1999 | Dickerhoff | ......... | 5/482 |
| 6,112,348 A * | 9/2000 | Dickerhoff | ......... | 5/482 |
| 6,167,885 B1 * | 1/2001 | Hanssen | ......... | 128/849 |
| 6,168,612 B1 * | 1/2001 | Augustine et al. | ......... | 607/107 |
| 6,176,870 B1 * | 1/2001 | Augustine | ......... | 607/107 |
| 6,203,567 B1 * | 3/2001 | Augustine | ......... | 607/104 |
| 6,820,622 B1 * | 11/2004 | Teves et al. | ......... | 128/849 |
| 6,994,720 B2 * | 2/2006 | Gammons | ......... | 607/104 |
| 7,096,870 B2 * | 8/2006 | Lamprich et al. | ......... | 128/849 |
| 7,108,713 B1 * | 9/2006 | Augustine | ......... | 607/107 |
| 7,172,616 B2 * | 2/2007 | Schuessler et al. | ......... | 607/107 |
| 7,409,953 B2 * | 8/2008 | Griesbach, III | ......... | 128/849 |
| 2003/0135251 A1 * | 7/2003 | Schuessler et al. | ......... | 607/104 |
| 2006/0052851 A1 * | 3/2006 | Anderson et al. | ......... | 607/104 |

(Continued)

*Primary Examiner*—Roy D Gibson
*Assistant Examiner*—Kaitlyn E Helling
(74) *Attorney, Agent, or Firm*—Fletcher Yoder

(57) ABSTRACT

A technique for heating a patient is provided. The technique includes providing a warming blanket comprising at least one section that can be moved relative to the remainder of the warming blanket to define an opening in the warming blanket. The technique also includes providing a drape suitable to cover the opening such that a seal is formed between the drape and the warming blanket along the periphery of the opening.

22 Claims, 5 Drawing Sheets

U.S. PATENT DOCUMENTS

| | | | |
|---|---|---|---|
| 2007/0093884 A1* | 4/2007 | Anderson et al. | 607/104 |
| 2008/0077207 A1* | 3/2008 | Vardanega | 607/107 |
| 2008/0077208 A1 | 3/2008 | Vardanega | |
| 2008/0077209 A1 | 3/2008 | Vardanega | |

* cited by examiner

USE OF CONVECTIVE AIR WARMING SYSTEM FOR PATIENT CARE

BACKGROUND OF THE INVENTION

1. Field of the Invention

The present disclosure is generally related to materials and procedures for maintaining patient temperature.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

A variety of medical environments are commonly maintained at temperatures well below body temperature to slow microbial growth, to counter the heat generated by medical lighting or equipment, or for various other reasons. For example, operating room temperatures of 65° F. (20° C.) and below are not uncommon. At such temperatures, it may be difficult to maintain the body temperature of the patient over time, such as over the course of a diagnostic, therapeutic, or surgical procedure.

For example, in a surgical context, a surgical drape may be employed to maintain the sterility of a portion of the patient's body undergoing an invasive procedure. However, such a drape may cause part of the patient's body (such as parts of the body under or proximate to the drape) to be exposed to the cool air of the operating room environment. Therefore, in such environments, it may be difficult to maintain a patient's body temperature.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a warming assembly. The warming assembly includes a warming blanket having at least one section that can be moved relative to the remainder of the warming blanket to define an opening in the warming blanket. The warming assembly also includes a drape suitable to cover the opening such that a seal is formed between the drape and the warming blanket along the periphery of the opening.

There is also provided a method for warming a patient. The method includes the act of placing a warming blanket on a patient. A movable section of the warming blanket is moved to an open position to expose a region on the patient. The region is covered with a drape such that a seal is formed between the warming blanket and the drape. Warmed air is provided to the warming blanket.

There is further provided a warming assembly. The warming assembly includes a warming blanket comprising an array of folding panels that can be moved relative to the remainder of the warming blanket. The warming assembly also includes a drape suitable to cover an opening defined by one or more of the folding panels when folded. A seal is formed between the drape and the warming blanket along the periphery of the opening.

BRIEF DESCRIPTION OF THE DRAWINGS

Some embodiments of the disclosure may be understood by referring, in part, to the following description and the accompanying drawings, in which like reference numbers refer to the same or like parts and wherein.

DETAILED DESCRIPTION OF SPECIFIC EMBODIMENTS

In some embodiments of the present technique, a warming blanket is employed that may be configured to allow access to different portions of a patient's body. For example, in one embodiment, the warming blanket may be used in conjunction with a surgical drape to allow a surgeon sterile access to a specific portion of a patient's body while allowing some or all of the remainder of the patient's body to be warmed.

Figure 1:
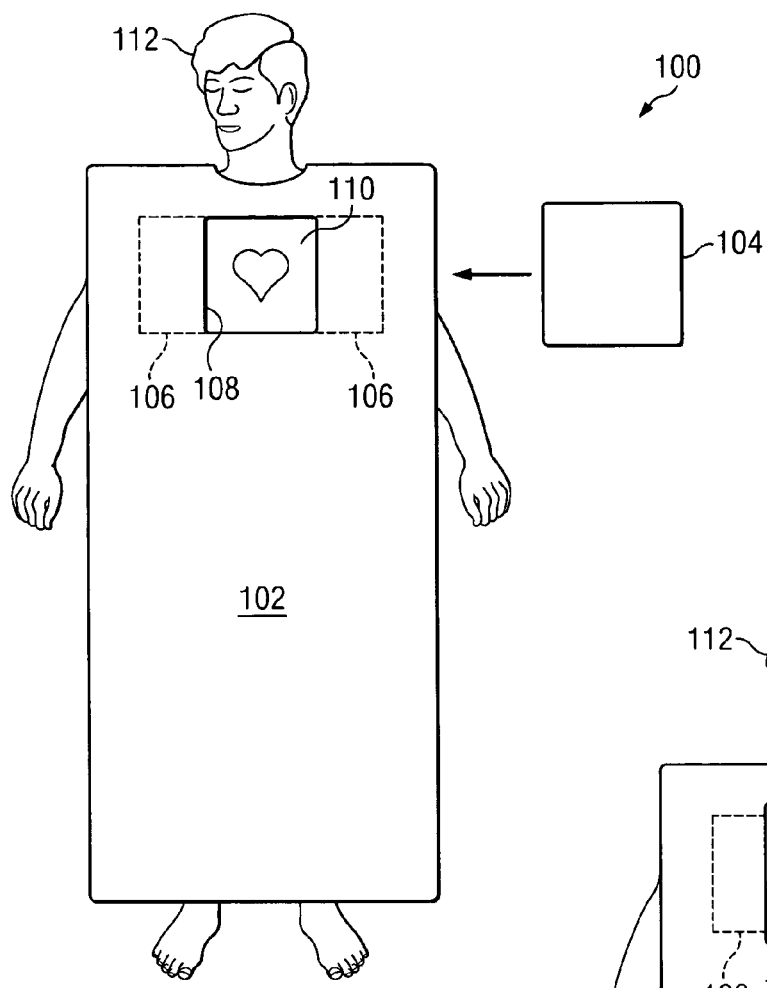
FIG. 1 depicts a patient covered by a warming blanket, in accordance with one embodiment of the present technique.

Referring now to FIG. 1, an embodiment of a warming assembly 100 is depicted. In the depicted embodiment, warming assembly 100 includes a warming blanket 102 and a drape 104, such as a sterile drape that may be suitable for use in surgery. Warming blanket 102, as depicted in FIG. 1, includes access panels 106. The access panels 106 are movable relative to the remainder of the warming blanket 102. For example, in one embodiment, the access panels 106 may be folded to define an opening 108. In an exemplary implementation, the opening 108 may be situated above a region 110 of patient 112. In this manner, access may be provided to the region 110 of the patient 112 to allow a medical procedure, such as a surgical procedure, to be performed on the region 110. Further, in such an exemplary implementation, all or part of the remainder of the patient's body remains covered by warming blanket 102. While the embodiment depicted in FIG. 1 depicts a configuration of access panels 106 suitable for cardiac surgery, one of ordinary skill in the art will appreciate that other embodiment may include more or fewer access panels 106 and access panels 106 located in different portions of warming blanket 102 to facilitate access to different regions of the patient's body.

Figure 2:
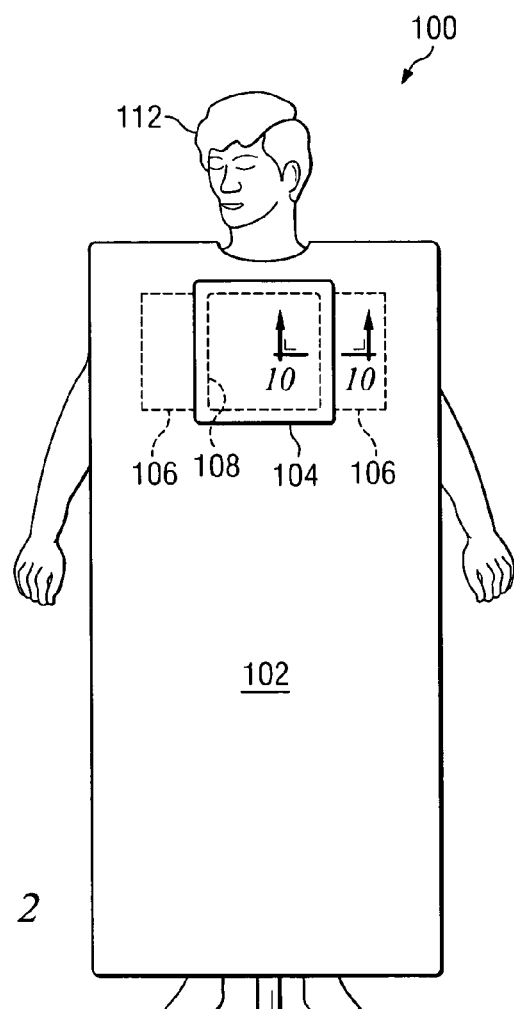
FIG. 2 depicts a patient heated by a warming assembly, in accordance with one embodiment of the present technique.

In an exemplary implementation, such as a surgical implementation, a drape 104 may be placed over the opening 108 in the warming blanket 102. Referring to FIG. 2, a warming assembly 100 is shown with drape 104 positioned over and covering all or part of opening 108 in the warming blanket 102. For example, in a surgical implementation, the drape 104 may be a transparent, pressure sensitive polyethylene film that is directly applied to the skin where the surgical incision is to be made. In such an implementation, the drape 104 is typically a sterile barrier to prevent infection of the incision site. In this type of exemplary surgical implementation the drape 104 is typically transparent so that the surgeon can make an incision through the drape 104.

As depicted in FIG. 2, the warming assembly 100 further includes a heated air blower 114. Heated air blower 114 is connected to the warming blanket 102 via hosing 116. As suggested by its name, heated air blower 114 produces and expels heated air. A commercially distributed device suitable for use as heated air blower 114 is the WarmTouch® 5200/5300 series of warming units from the Nellcor division of Tyco Healthcare. For example, in an embodiment of warming assembly 100 that implements heated air blower 114 with a WarmTouch® 5300 warming unit, heated air may be provided to warming blanket 102 at predefined temperatures of 32° C., 38° C., 43°, or 45° C. In the depicted embodiment, heated air from heated air blower 114 is provided to warming blanket 102 through the hosing 116 via an entry port or other opening in warming blanket 102 as described in greater detail below.

Figure 3:
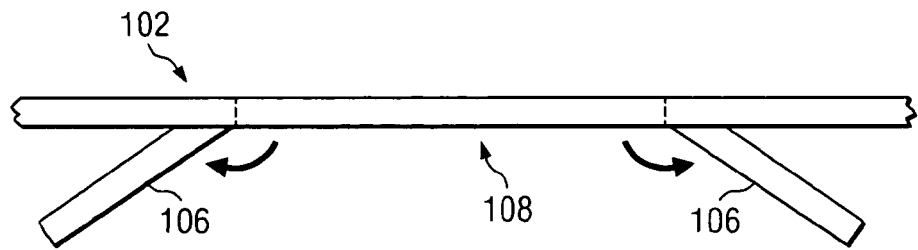
FIG. 3 is a side view of a surgical blanket having folding access panels, in accordance with aspects of the present technique.
Figure 4:
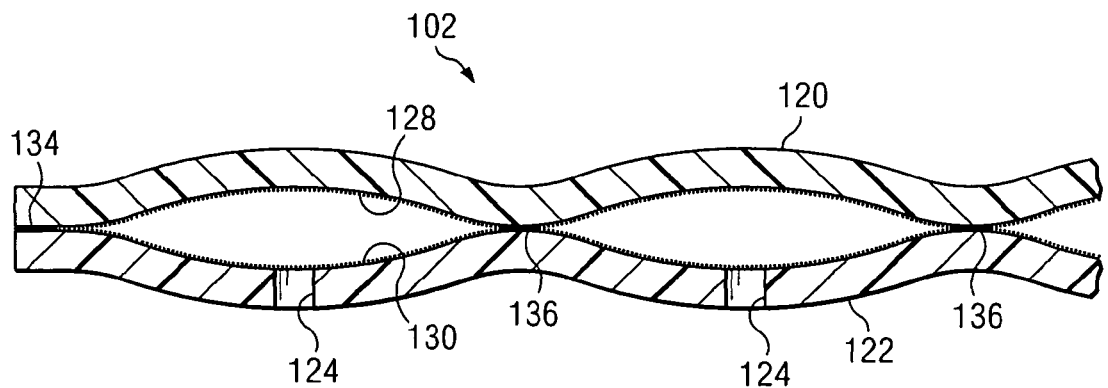
FIG. 4 is a cross-sectional view of a surgical blanket depicting internal welds and vent holes, as seen from view line 4 of FIG. 1, in accordance with one embodiment of the present technique.

Turning now to FIG. 3, the warming blanket 102 is shown in a front view with the access panels 106 folded to create opening 108 in the warming blanket 102. Referring to FIG. 4, a cross-section of warming blanket 102, taken along view line 4 of FIG. 1, is shown as including a first sheet 120 and a second sheet 122. In the depicted embodiment, the second sheet 122 includes vent holes 124 through which the heated air exits the warming blanket 102. As will be appreciated by those of ordinary skill in the art, the vent holes 124 may be provided in a uniform or other pattern on one of first and/or second sheet 120, 122.

In one embodiment, the first sheet 120 includes a layer of a polypropylene material and the second sheet 122 includes a layer of a polyester. As will be appreciated by those of ordinary skill in the art, other materials, including other polymeric materials, other organic materials, and/or naturally occurring materials (such as cotton) may be included in the first and/or second sheets 120 and 122.

In some embodiments, the first and/or second sheets 120 and 122 also include bonding layers or films, 128, 130, typically applied to the respective interior surfaces of the first and second sheets 120, 122. Such bonding layers 128, 130 may be applied to the first and/or second sheets 120, 122 by spraying, sputtering, or other techniques known in the art for depositing a layer or film of material on a substrate. The bonding layers 128, 130 may be employed in embodiments where attachments between the first and second sheets 120, 122 are not easily formed, such as due to the compositions of the first and second sheets 120, 122. In such embodiments, bonding layers 128, 130 may be selected and employed that can be adhered to both the first and second sheets 120, 122 and that can form attachments between the bonding layers 128 and 130. For example, in one embodiment the bonding layers 128, 130 are polyethylene films that are sprayed on to the respective first and second sheets 120, 122. Such polyethylene films typically can be applied to the compositions forming the first and second sheets 120, 122 and can be adhered to one another using conventional heating and/or welding techniques, as described below.

The first and second sheets 120 and 122 are joined along their peripheries by a seal 134 that extends around the perimeter of the warming blanket 102. In the depicted embodiment, the seal 134 forms an air tight barrier around the perimeter of warming blanket 102 so that air entering between sheets 120 and 122 from the heated air blower 114 (depicted in FIG. 2) does not escape warming blanket 102 at its perimeter, but instead exits via the vent holes 124 provided on the surface of the warming blanket 102. The seal 134 may be formed using heat and/or pressure to bond the respective bonding layers 128, 130 of the first and second sheets 120, 122 (or the respective first and second sheets 120, 122 themselves, were possible) together along the perimeter of the warming blanket 102. Alternatively, in other embodiments, the seal 134 may be formed using an adhesive to adhere the first and second sheets 120, 122 along the perimeter of the warming blanket 102.

Interior to the perimeter of warming blanket 102, multiple instances of weld points 136 are depicted. Weld points 136 represent interior locations in the warming blanket 102 where the first sheet 120 is attached to the second sheet 122. By providing a plurality of welds 136 throughout the interior portions of warming blanket 102, air entering warming blanket 102 between sheets 120 and 122 creates a quilted effect in which the unwelded portions of sheets 120 and 122, i.e., the spaces, surrounding welds 136 may expand without becoming unattached. As with the seals 134, the welds 136 may be formed by locally heating regions of warming blanket 102 to bond the respective bonding layers 128, 130 together. In one embodiment, localized heating causes polyethylene on first and second sheets 120 and 122 to adhere to one another, thereby creating weld points 136.

Although warming blanket 102 has been described herein as comprising two distinct sheets sealed together at their perimeter, other embodiments may employ a different construction. For example, in other embodiments, the warming blanket 102 may be formed as a single continuous sheet that is folded and sealed or a single continuous bag or pouch. Moreover, the quilted effect described herein may be achieved using means other than localized welds 136. For example, an adhesive material may be applied selectively to the interior surfaces of warming blanket 102 to form localized attachments.

In one embodiment, the composition of the first sheet 120, such as polypropylene, may be selected to provide a durable and/or a tear resistant material that can withstand the patient's environment, such as an operating room environment. The composition of the second sheet 122, such as polyester, may be selected to provide patient comfort. For example, in one embodiment, polymer materials are used in the second sheet 122. However, in other embodiments, naturally occurring or woven materials, such as cotton and other fibers, may be used in the second sheet 122.

Referring now to FIGS. 5 through 9, a specific implementation of a warming blanket 102 is depicted in top view (FIG. 5) and multiple detail views (FIGS. 6 through 9). In the depicted embodiment of FIG. 5, the warming blanket 102 is substantially rectangular in shape. As will be appreciated by those of ordinary skill in the art, other geometries and configurations of the warming blanket 102 are also within the scope of the present disclosure. In one embodiment, the overall length of warming blanket 102 is in the range of about 72 to about 84 inches (about 1.83 m to about 2.13 m) while the overall width is in the range of about 36 to about 48 inches (about 0.914 m to about 1.219 m). These dimensions are typically sufficient to enable warming blanket 102 to substantially cover a patient's body during a medical procedure, such as surgery, while permitting medical personnel access to the patient via the openings 108 provided by the present techniques.

Figure 6:
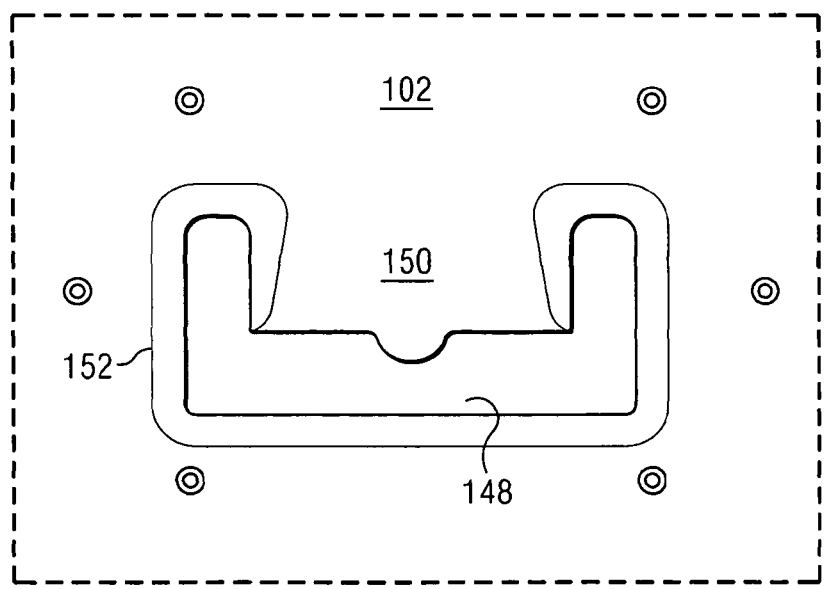
FIG. 6 is a detail view of the air inlet region of the warming blanket depicted in the embodiment of FIG. 5.

An air inlet 144, depicted in the detail view of FIG. 6, is provided in the warming blanket 102. The air inlet 144 provides a port into which blower 114 (FIG. 2) may blow heated air. In the embodiment depicted in FIGS. 5 and 6, the air inlet 144 is implemented as a U-shaped cut-out 148 in warming blanket 102 that results in the creation of an inlet flange 150. An inlet seal 152 seals first and second sheets 120 and 122 (FIG. 4) along the edges of the U-shaped cut-out 148 except along the inlet defined by the inlet flange 150. The absence of a seal between sheets 120 and 122 along the inlet flange 150 enables sheets 120 and 122 to be separated sufficiently to receive hosing 116 (FIG. 2) so that heated air from heated air blower 114 can be blown into the warming blanket 102.

The depicted implementation of warming blanket 102 includes an array 154 of foldable panels 156. In the depicted embodiment of FIG. 7, each panel 156 is substantially rectangular in shape and is circumscribed on three of four sides by perforations 158. The edges of the panels 156 are sealed proximate to the perforations to prevent loss of heated air within the blanket during use.

Figure 5:
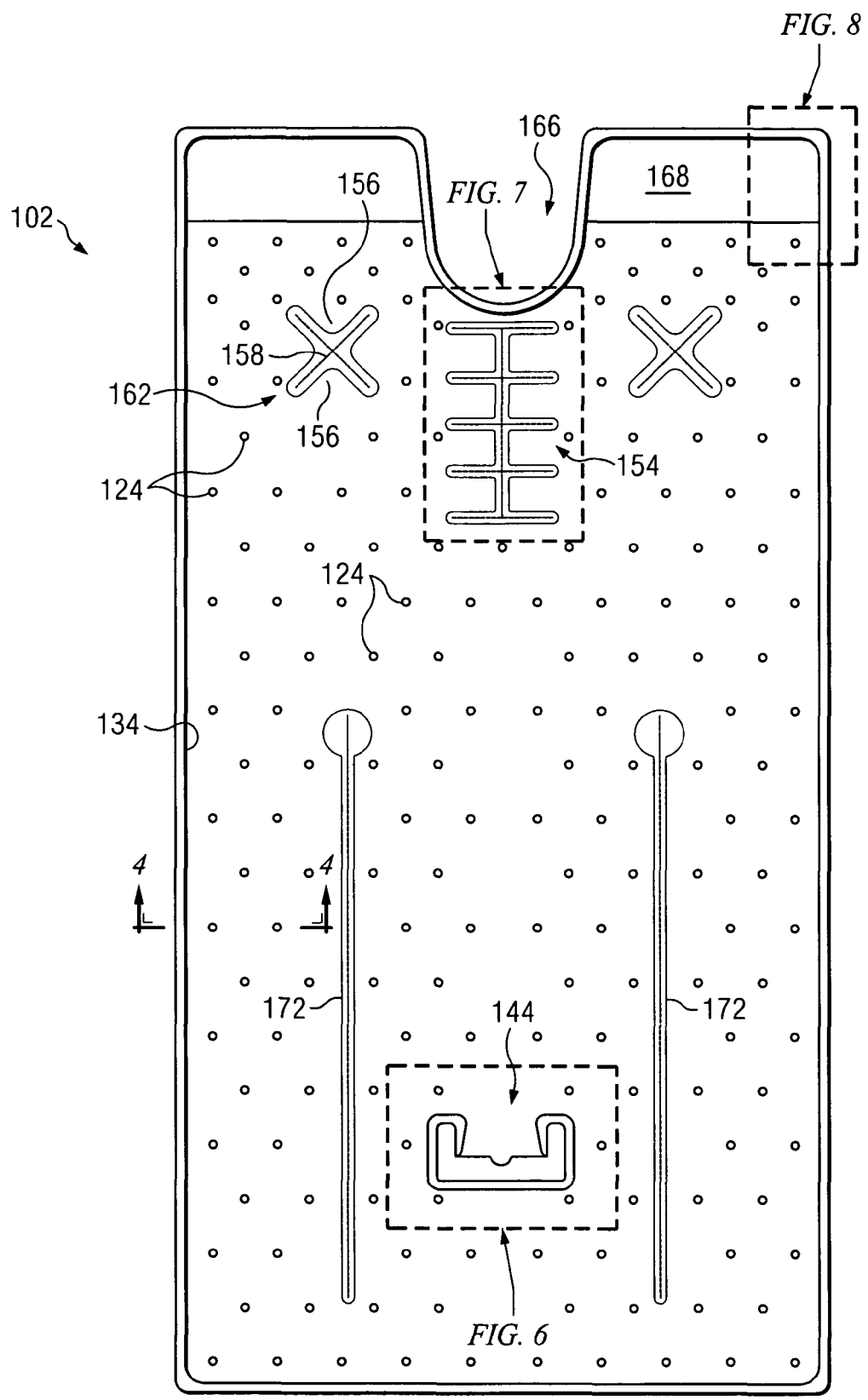
FIG. 5 is a top view of one embodiment of a warming blanket, in accordance with one embodiment of the present technique.
Figure 7:
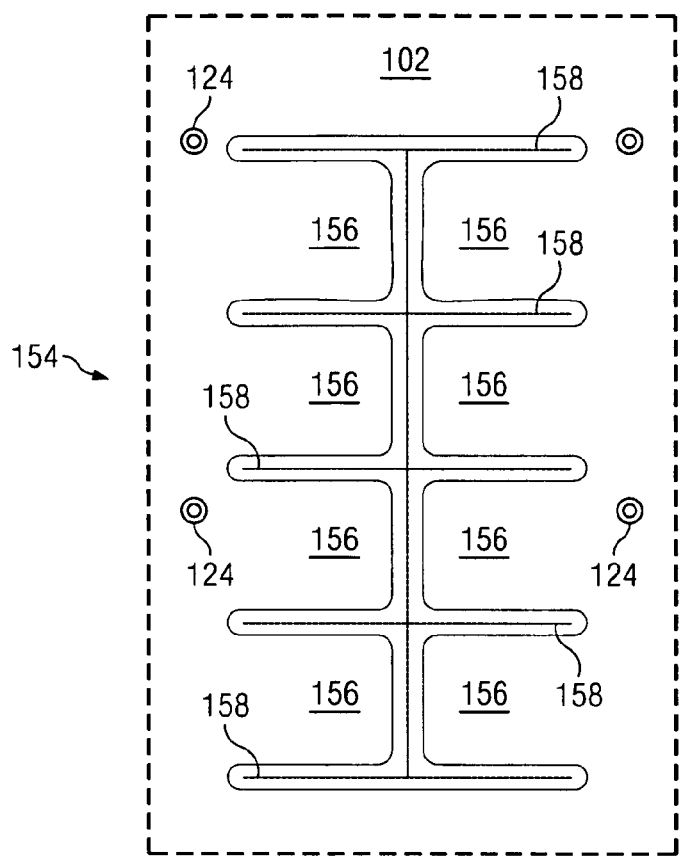
FIG. 7 is a detail view of one array of folding access panels of the warming blanket depicted in the embodiment of FIG. 5.
Figure 8:
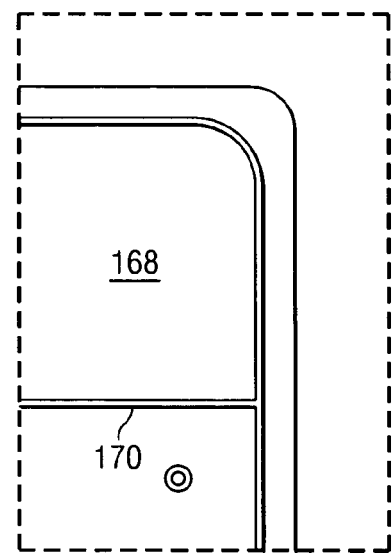
FIG. 8 is a detail view of the corner of the warming blanket depicted in the embodiment of FIG. 5.

By breaking one or more of the perforations 158 and folding back the respective panels 156, medical personnel, such as an operating room attendant, can create an opening in the warming blanket 102, such as the opening 108 depicted in FIG. 1. By implementing warming blanket 102 with such an array 154 of panels 156, medical personnel may create an opening 108 in the warming blanket 102 that is suitable in size to perform a desired procedure, such as a surgical operation. Although the depicted implementation of panel array 154 employs a 4×2 array of panels 156, other implementations may employ different configurations of arrays and panels. For example, warming blanket 102 as depicted in FIG. 5 includes a second panel array 162 that includes four foldable panels 156, here depicted as triangular panels, separated by a perforation 158. With second panel array 162, any or all of the foldable panels 156 may be folded back by breaking perforation 158 along two sides of the corresponding triangular panel to form a corresponding warming blanket opening. In the depicted embodiment, the second panel arrays 162 (of which two are shown) are positioned for use in a procedure in the vicinity of a patient's shoulders (e.g., a collar bone procedure).

In the depicted embodiment, a cut-out region 166 is provided at one end of the warming blanket 102. In this embodiment, the cut-out 166 conforms to a patient's neck, thereby permitting the warming blanket 102 to be placed over a patient's shoulders without covering the patient's face. Warming blanket 102 as implemented in FIG. 5 includes flaps 168 located on either side of cut-out 166. As depicted in greater detail in FIG. 8, flaps 168 are separated from the remainder of the warming blanket 102 by a seal 170 that prevents air from blower 114 from entering flaps 168 so that the flaps are not inflated when warming blanket 102 is in use. In such an embodiment, flaps 168 may be folded under a patient's shoulders to secure the warming blanket and to reduce heat loss from the patient.

Figure 9:
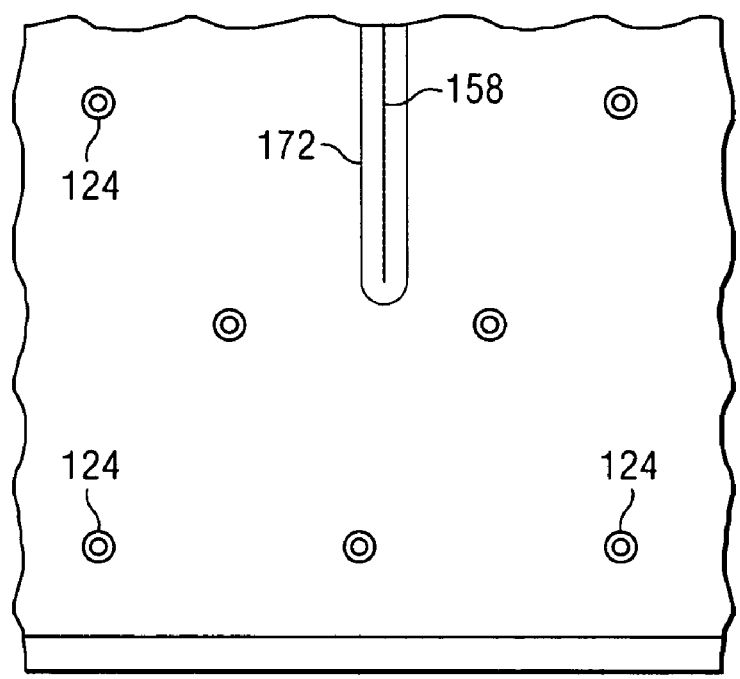
FIG. 9 is a detail view of a portion of a leg hole of the warming blanket depicted in the embodiment of FIG. 5.

The depicted embodiment of warming blanket 102 further includes leg openings 172, depicted in greater detail in FIG. 9. In the depicted embodiment, leg openings 172 are provided as elongated perforations 158 in the warming blanket 102 that may be broken to allow a leg of a patient to pass through the warming blanket 102. In one embodiment of the warming blanket 102, the length of the leg openings 172 is in the range of about 24 to about 40 inches (about 61.0 cm to about 101.6 cm).

Figure 10:
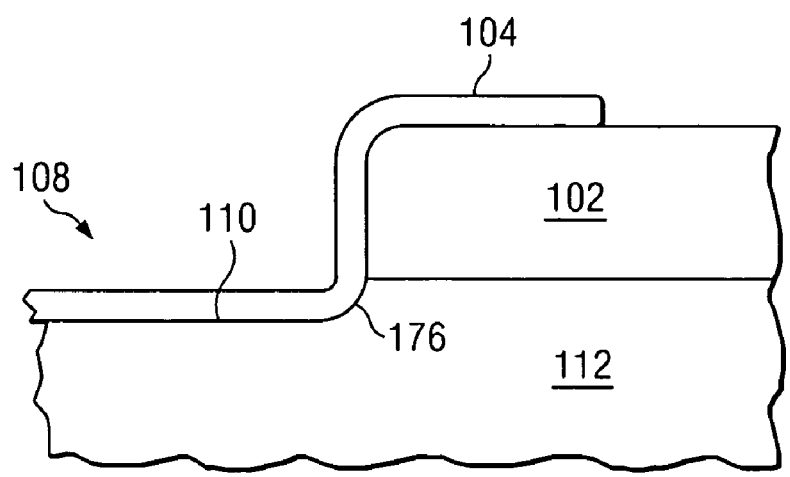
FIG. 10 is a partial cross-sectional view of a warming blanket and drape on a patient, as seen from view line 10 of FIG. 2, in accordance with one embodiment of the present technique.

In one implementation, the warming blanket 102 is placed on a patient, such as prior to surgery, and one or more panels 156 are folded or otherwise moved to form an opening 108 in the warming blanket 102. In such an implementation, the opening may be positioned to expose a region 110 of the patient for which access is need (such as a surgical site) while leaving most or all of the remainder of the patient covered with warming blanket 102. In some embodiments, a drape 104, such as a surgical drape, is placed over the opening 108 in warming blanket 102 and a portion of the drape 104 is affixed to or sealed against the warming blanket 102. For example, referring now to FIG. 10 which depicts a cross-sectional view taken along view line 10 of FIG. 2, a portion of the drape 104 overlying opening 108 and region 110 of the patient 112 is applied to the skin of the patient and forms a seal 176 along the boundary defined by the patient 112 and the warming blanket 102. The seal 176 forms a perimeter barrier around the region 110 in which a medical procedure is to be performed, such as a surgical site. A blower 114 provides warmed air to warming blanket 102 which may inflate the warming blanket 102 and, upon exiting the warming blanket 102, may generally warm the patient's body. In one embodiment, placing the warming blanket 102 over the patient covers the patient 112 between the patient's neck region and the patient's ankle region thereby covering substantially all of the patient's body except for that portion exposed through the one or more openings 108.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A warming assembly, comprising:
   a warming blanket comprising at least one section that can be moved relative to the remainder of the warming blanket to define an opening in the warming blanket; and
   a drape suitable to cover the opening such that a seal is formed between the drape and the warming blanket along the periphery of the opening.

2. The warming assembly of claim 1, comprising a heated air blower configured to provide heated air to the warming blanket.

3. The warming assembly of claim 1, wherein the at least one sections are provided as one or more arrays of sections.

4. The warming assembly of claim 1, wherein each section is defined by perforations that, once broken, allow the respective section to move relative to the remainder of the warming blanket.

5. The warming assembly of claim 1, wherein the drape comprises a sterile drape suitable for surgery.

6. The warming assembly of claim 1, wherein the warming blanket comprises a first sheet and a second sheet.

7. The warming assembly of claim 6, wherein the first sheet and the second sheet are sealed together along a common perimeter.

8. The warming assembly of claim 6, wherein the first and second sheet are attached by welds within the interior of the warming blanket.

9. The warming assembly of claim 6, wherein the first sheet comprises a polypropylene composition and the second sheet comprises a polyester composition.

10. The warming assembly of claim 6, wherein a polyethylene film covers interior surfaces of the first sheet and the second sheet.

11. A method for warming a patient, comprising:
placing a warming blanket on a patient;
moving a movable section of the warming blanket to an open position to expose a region on the patient;
covering the region with a drape such that a seal is formed between the warming blanket and the drape; and
providing warmed air to the warming blanket.

12. The method of claim 11, wherein moving the movable section comprises folding at least one panel in an array of panels.

13. The method of claim 11, comprising breaking one or more perforations proximate to the movable section.

14. The method of claim 11, wherein providing warmed air to the warming blanket comprises blowing warmed air into an interior space defined by a first sheet and a second sheet sealed together along their perimeters.

15. A warming assembly, comprising:
a warming blanket comprising an array of folding panels that can be moved relative to the remainder of the warming blanket; and
a drape suitable to cover an opening defined by one or more of the folding panels when folded, wherein a seal is formed between the drape and the warming blanket along the periphery of the opening.

16. The warming assembly of claim 15, comprising a heated air blower configured to provide heated air to the warming blanket.

17. The warming assembly of claim 15, wherein each folding panel is defined by perforations that, once broken, allow the respective folding panel to move relative to the remainder of the warming blanket.

18. The warming assembly of claim 15, wherein the drape comprises a sterile drape suitable for surgery.

19. The warming assembly of claim 15, wherein the warming blanket comprises a multi-layer structure.

20. The warming assembly of claim 19, wherein the multi-layer structure is sealed together along its perimeter.

21. The warming assembly of claim 19, wherein the multi-layer structure is internally attached by welds.

22. The warming assembly of claim 19, wherein the multi-layer structure comprises a polypropylene layer and a polyester layer.

* * * * *